(12) United States Patent
Angell et al.

(10) Patent No.: US 7,396,843 B2
(45) Date of Patent: Jul. 8, 2008

(54) 5'-CARBAMOYL-1,1'-BIPHENYL-4-CARBOXAMIDE DERIVATIVES AND THEIR USE AS P38 KINASE INHIBITORS

(75) Inventors: Richard Martyn Angell, London (GB); Nicola Mary Aston, Stevenage (GB); Paul Bamborough, Stevenage (GB); Mark James Bamford, Harlow (GB); George Stuart Cockerill, London (GB); Suzanne Joy Merrick, London (GB); Ann Louise Walker, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 423 days.

(21) Appl. No.: 10/492,699

(22) PCT Filed: Oct. 16, 2002

(86) PCT No.: PCT/EP02/11573

§ 371 (c)(1),
(2), (4) Date: Oct. 12, 2004

(87) PCT Pub. No.: WO03/032980

PCT Pub. Date: Apr. 24, 2003

(65) Prior Publication Data

US 2005/0038014 A1     Feb. 17, 2005

(30) Foreign Application Priority Data

Oct. 17, 2001    (GB)    ................................. 0124931.7

(51) Int. Cl.
*A61K 31/44* (2006.01)
*A61K 31/42* (2006.01)
*C07D 401/00* (2006.01)
*C07D 261/02* (2006.01)
*C07D 333/22* (2006.01)

(52) U.S. Cl. ...................... 514/343; 514/378; 514/408; 514/438; 514/461; 546/276.4; 548/240; 549/70; 549/497

(58) Field of Classification Search ................. 514/343, 514/378, 408, 438, 461; 546/276.4; 548/240; 549/70, 497
See application file for complete search history.

(56) References Cited

U.S. PATENT DOCUMENTS

| | | | |
|---|---|---|---|
| 4,200,750 A | 4/1980 | Warner et al. | |
| 4,968,804 A | 11/1990 | Stanek et al. | |
| 5,064,832 A | 11/1991 | Stanek et al. | |
| 5,236,934 A | 8/1993 | VanAtten | |
| 5,246,943 A | 9/1993 | Blankley et al. | |
| 5,521,213 A | 5/1996 | Prasit et al. | |
| 5,534,518 A | 7/1996 | Henrie et al. | |
| 5,658,903 A | 8/1997 | Adams et al. | |
| 5,858,995 A | 1/1999 | Kawai et al. | |
| 5,877,190 A | 3/1999 | Dhainaut et al. | |

(Continued)

FOREIGN PATENT DOCUMENTS

| | | |
|---|---|---|
| EP | 0 533 268 | 9/1992 |
| EP | 0 533 266 | 3/1993 |
| EP | 0 849 256 | 6/1998 |
| EP | 0 346 841 | 6/2003 |
| EP | 0 430 033 | 4/2004 |
| GB | 2 276 161 | 3/1993 |
| GB | 2 273 930 | 12/1993 |
| GB | 2 276 161 | 9/1994 |
| GB | 2 276 162 | 9/1994 |
| GB | 2 295 387 | 5/1996 |
| JP | 11218884 | 8/1999 |
| WO | WO 94/15920 | 7/1994 |

(Continued)

OTHER PUBLICATIONS

U.S. Appl. No. 10/492,715.*
Copending U.S. Appl. Nos. 10/492,711; 10/551,502; 10/568,121; 10/551,502; 11/556,285.*
Boehm et al., *Expert Opinion of Therapeutic Patents*, vol. 10 (1) pp. 25-37 (2000).
Boehm, et al, *Journal of Medicinal Chemistry*, vol. 39(20) pp. 3929-3937 (1996).
Ceccarelli et al., *European Journal of Medicinal Chemistry*, vol. 33 (12) pp. 943-955 (1998).
Gabriele et al., *European Journal of Organic Chemistry*, vol. 2001 (24) pp. 4607-4613 (2001).

(Continued)

*Primary Examiner*—Joseph McKane
*Assistant Examiner*—Susannah Chung
(74) *Attorney, Agent, or Firm*—Dara L. Dinner; Stephen Venetianer; Charles M. Kinzig

(57) ABSTRACT

Compounds of formula (I):

or pharmaceutically acceptable salts or solvates thereof, and their use as pharmaceuticals, particularly as p38 kinase inhibitors.

20 Claims, No Drawings

U.S. PATENT DOCUMENTS

| | | | |
|---|---|---|---|
| 5,932,576 | A | 8/1999 | Anantanarayan et al. |
| 5,945,418 | A | 8/1999 | Bemis et al. |
| 5,977,103 | A | 11/1999 | Adams et al. |
| 6,060,491 | A | 5/2000 | Pruitt et al. |
| 6,080,767 | A * | 6/2000 | Klein et al. .................. 514/357 |
| 6,087,496 | A | 7/2000 | Anantanarayan et al. |
| 6,130,235 | A | 10/2000 | Mavunkel et al. |
| 6,147,080 | A | 11/2000 | Bemis et al. |
| 6,174,887 | B1 | 1/2001 | Haruta et al. |
| 6,251,914 | B1 | 6/2001 | Adams et al. |
| 6,277,989 | B1 | 8/2001 | Chakravarty et al. |
| 6,323,227 | B1 | 11/2001 | Klein et al. |
| 6,376,546 | B1 | 4/2002 | Shoda et al. |
| 6,392,047 | B1 | 5/2002 | Geissler et al. |
| 6,399,627 | B1 | 6/2002 | Song et al. |
| 6,420,561 | B1 | 7/2002 | Haruta et al. |
| 6,436,925 | B1 | 8/2002 | Lubisch et al. |
| 6,448,257 | B1 | 9/2002 | Mavunkel et al. |
| 6,451,794 | B1 | 9/2002 | Beswick et al. |
| 6,498,166 | B1 | 12/2002 | Campbell et al. |
| 6,509,361 | B1 | 1/2003 | Weier et al. |
| 6,509,363 | B2 | 1/2003 | Salituro et al. |
| 6,545,054 | B1 | 4/2003 | Song et al. |
| 6,576,632 | B1 | 6/2003 | Goldstein et al. |
| 6,579,872 | B1 | 6/2003 | Brown et al. |
| 6,605,625 | B2 | 8/2003 | Peukert et al. |
| 6,638,980 | B1 | 10/2003 | Su et al. |
| 6,696,464 | B2 | 2/2004 | McClure et al. |
| 6,699,994 | B1 | 3/2004 | Babu et al. |
| 6,774,127 | B2 | 8/2004 | Adams et al. |
| 6,794,377 | B2 | 9/2004 | Peukert et al. |
| 6,821,965 | B1 | 11/2004 | Brown et al. |
| 6,855,719 | B1 | 2/2005 | Thomas et al. |
| 6,867,209 | B1 | 3/2005 | Mavunkel et al. |
| 6,924,392 | B2 | 8/2005 | Peukert et al. |
| 6,936,719 | B2 | 8/2005 | Babu et al. |
| 6,956,037 | B2 | 10/2005 | Brown et al. |
| 7,125,898 | B2 * | 10/2006 | Aston et al. .................. 514/355 |
| 7,151,118 | B2 * | 12/2006 | Angell et al. ............... 514/617 |
| 7,166,623 | B2 | 1/2007 | Angell et al. |
| 2001/0011135 | A1 | 8/2001 | Reidl et al. |
| 2003/0055088 | A1 | 3/2003 | Shao et al. |
| 2003/0139605 | A1 | 7/2003 | Riedl et al. |
| 2003/0225089 | A1 | 12/2003 | Jung et al. |
| 2004/0038858 | A1 | 2/2004 | Dorsch et al. |
| 2004/0053942 | A1 | 3/2004 | Alberti et al. |
| 2004/0116479 | A1 | 6/2004 | Haviv et al. |
| 2004/0128287 | A1 | 7/2004 | Barth et al. |
| 2004/0138287 | A1 | 7/2004 | Takeuchi et al. |
| 2004/0162281 | A1 | 8/2004 | Babu et al. |
| 2004/0176446 | A1 | 9/2004 | Alonso-Alija et al. |
| 2004/0242868 | A1 | 12/2004 | Angell et al. |
| 2004/0249161 | A1 | 12/2004 | Angell et al. |
| 2004/0254200 | A1 | 12/2004 | Davis et al. |
| 2004/0266839 | A1 | 12/2004 | Angell et al. |
| 2004/0267012 | A1 | 12/2004 | Angell et al. |
| 2005/0020540 | A1 | 1/2005 | Angell et al. |
| 2005/0020590 | A1 | 1/2005 | Lang et al. |
| 2005/0065195 | A1 | 3/2005 | Angell et al. |
| 2005/0090491 | A1 | 4/2005 | Angell et al. |
| 2006/0089393 | A1 | 4/2006 | Angell et al. |
| 2006/0122221 | A1 | 6/2006 | Angell et al. |
| 2006/0241179 | A1 | 10/2006 | Aston |
| 2006/0264479 | A1 | 11/2006 | Aston et al. |
| 2006/0276516 | A1 | 12/2006 | Aston et al. |

FOREIGN PATENT DOCUMENTS

| | | |
|---|---|---|
| WO | WO 95/06636 | 3/1995 |
| WO | WO 95/06644 | 3/1995 |
| WO | WO 95/11243 | 4/1995 |
| WO | WO 95/15954 | 6/1995 |
| WO | WO 95/17401 | 6/1995 |
| WO | WO 95/29907 | 11/1995 |
| WO | WO 95/30675 | 11/1995 |
| WO | 96/31508 | 10/1996 |
| WO | WO 96/31508 | 10/1996 |
| WO | WO 96/31509 | 10/1996 |
| WO | WO 97/03034 | 1/1997 |
| WO | WO 98/57934 | 12/1998 |
| WO | WO 99/32463 | 7/1999 |
| WO | WO 00/12074 | 3/2000 |
| WO | WO 00/12497 | 3/2000 |
| WO | WO 00/26216 | 5/2000 |
| WO | 00/41698 | 7/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 01/27089 | 4/2001 |
| WO | WO 01/34605 | 5/2001 |
| WO | WO 01/70695 | 9/2001 |
| WO | WO 01/87875 | 11/2001 |
| WO | WO 02/40486 | 5/2002 |
| WO | WO 03/032970 | 4/2003 |
| WO | WO 03/068747 | 8/2003 |
| WO | WO 03/093248 | 11/2003 |
| WO | WO 2004/010995 | 2/2004 |
| WO | WO 2004/089874 | 10/2004 |
| WO | WO 2004/089875 | 10/2004 |
| WO | WO 2004/089876 | 10/2004 |
| WO | WO 2005/014550 | 2/2005 |
| WO | WO 2006/110173 | 10/2006 |

OTHER PUBLICATIONS

Han et al., *Biohemica et Biophysica Acta—Molecular Cell Research*, vol. 1265 (2-3) pp. 224-227 (1995.
Hanson, *Expert Opinion on Therapeutic Patents*, vol. 7(7) pp. 729-733 (1997).
Henry et al., *Drugs of the Future*, vol. 24 (12) pp. 1345-1354 (1999).
Jiang et al, *Journal of Biological Chemistry*, vol. 271 (30) pp. 17920-17926 (1996).
Li et al., *Biochemical and Biophysical Research Communications*, vol. 228 (2) pp. 334-340 (1996).
Liebeskind et al., *Organic Letters*, vol. 4 (6) pp. 979-981 (2002).
Moreland et al., *Annals of Internal Medicine*, vol. 130 (6) pp. 478-486 (1999).
Murali Dhar et al., *Bioorganic and Medicinal Chemistry Letters*, vol. 12 (21) pp. 3125-3128 (2002).
Rankin et al., *British Journal of Rheumatology*, vol. 34 pp. 334-342 (1995).
Salituro et al., *Current Medicinal Chemistry*, vol. 6 pp. 807-823 (1999).
Wang et al., *Journal of Biological Chemistry*, vol. 272 (38) pp. 23668-23674 (1997).
Angell et al.; U.S. Appl. No. 10/492,714, filed Apr. 15, 2004.
Walker, A. U.S. Appl. No. 10/568,121, filed Feb. 9, 2006.
Aston, N.; U.S. Appl. No. 10/551,503, filed Sep. 30, 2005.
Aston, et al.; U.S. Appl. No. 10/551,502, filed Sep. 30, 2005.
Campos, et al., U.S. Appl. No. 10/587,614, filed Jan. 27, 2005.
Patel, et al., U.S. Appl. No. 10/587,613, filed Jan. 27, 2005.
Bamborough, et al., U.S. Appl. No. 10/587,790, filed Jan. 27, 2005.
Barker, et al., U.S. Appl. No. 10/587,989, filed Jan. 27, 2005.
Angell et al., U.S. Appl. No. 11/557,607, filed Nov. 8, 2006.
Angell et al., U.S. Appl. No. 11/556,285, filed Nov. 3, 2006.
Angell et al., U.S. Appl. No. 11/669,219, filed Jan. 31, 2007.
Courtney, S. et al., *Bioorganic & Medicinal Chemistry Letters*, vol. 14 pp. 3269-3273 (2004).
Foster, et al., *Drug News Perspect.*, vol. 13(8) pp. 488-497 (2000).
Henry, et al., *Bioorganic & Medicinal Chemistry Letters*, vol. 8 pp. 3335-3340 (1998).

Herlaar, et al., Molecular Medicine Today, vol. 5 pp. 439-447 (1999).
Marin, et al., *Blood*, vol. 98(3) pp. 667-673 (2001).
Underwood, et al., *Journal of Pharmacology and Experimental Therapeutics*, vol. 293 (1) pp. 281-288 (2000).

Wadsworth, et al., Journal of Pharmacology and Experimental Therapeutics, vol. 291(2) pp. 680-687 (1999).

* cited by examiner

5'-CARBAMOYL-1,1'-BIPHENYL-4-CARBOXAMIDE DERIVATIVES AND THEIR USE AS P38 KINASE INHIBITORS

This application is filed pursuant to 35 U.S.C. §371 as a United States National Phase Application of International Application No. PCT/EP02/11573 filed Oct. 16, 2002, which claims priority from GB 0124931.7 filed Oct.

This invention relates to novel compounds and their use as pharmaceuticals, particularly as p38 kinase inhibitors, for the treatment of certain diseases and conditions.

We have now found a group of novel compounds that are inhibitors of p38 kinase.

According to the invention there is provided a compound of formula (I):

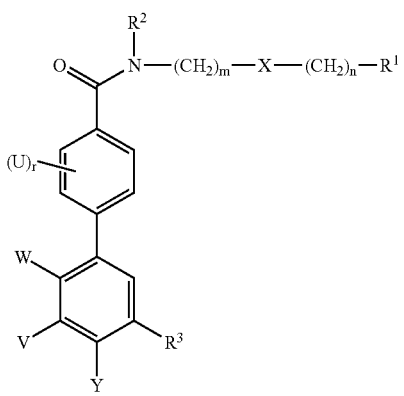

(I)

wherein

X is a bond or a phenyl group which may be optionally substituted;

$R^1$ is selected from an optionally substituted five- to seven-membered heterocyclic ring, an optionally substituted five- to seven-membered heteroaryl ring and an optionally substituted fused bicyclic ring;

$R^2$ is selected from hydrogen, $C_{1-6}$alkyl and —$(CH_2)_p$—$C_{3-7}$cycloalkyl;

or when X is a bond and m and n are both zero, $R^1$ and $R^2$, together with the nitrogen atom to which they are bound, form a five- to six-membered heterocyclic ring optionally containing one additional heteroatom selected from oxygen and nitrogen, which can be optionally substituted by $C_{1-4}$alkyl;

$R^3$ is the group —CO—NH—$(CH_2)_q$—$R^4$;

when q is 0 to 2 $R^4$ is selected from hydrogen, $C_{1-6}$alkyl, —$C_{3-7}$cycloalkyl, $CONHR^5$, phenyl optionally substituted by $R^7$ and/or $R^8$, heteroaryl optionally substituted by $R^7$ and/or $R^8$ and heterocyclyl optionally substituted by $R^7$ and/or $R^8$;

and when q is 2 $R^4$ is additionally selected from $C_{1-6}$alkoxy, $NHCOR^5$, $NHCONHR^5$, $NR^5R^6$, and OH;

$R^5$ is selected from hydrogen, $C_{1-6}$alkyl and phenyl wherein the phenyl group may be optionally substituted by up to two substituents selected from $C_{1-6}$alkyl and halogen;

$R^6$ is selected from hydrogen and $C_{1-6}$alkyl;

or $R^5$ and $R^6$, together with the nitrogen atom to which they are bound, form a five- to six-membered heterocyclic or heteroaryl ring optionally containing one additional heteroatom selected from oxygen, sulfur and nitrogen, wherein the ring may be substituted by up to two $C_{1-6}$alkyl groups;

$R^7$ is selected from $C_{1-6}$alkyl, $C_{1-6}$alkoxy, —$CONR^6R^9$, —$NHCOR^9$, —$SO_2NHR^9$, —$NHSO_2R^9$, halogen, trifluoromethyl, -Z-$(CH_2)_s$-phenyl optionally substituted by one or more halogen atom, -Z-$(CH_2)_s$-heterocyclyl or -Z-$(CH_2)_s$-heteroaryl wherein the heterocyclyl or heteroaryl group may be optionally substituted by one or more substituents selected from $C_{1-6}$alkyl;

$R^8$ is selected from $C_{1-6}$alkyl and halogen;

or when $R^7$ and $R^8$ are ortho substituents, then together with the carbon atoms to which they are bound, $R^7$ and $R^8$ may form a five- or six-membered saturated or unsaturated ring to give a fused bicyclic ring system, wherein the ring that is formed by $R^7$ and $R^8$ may optionally contain one or two heteroatoms selected from oxygen, nitrogen and sulfur;

$R^9$ is selected from hydrogen and $C_{1-6}$alkyl;

U is selected from methyl and halogen;

W is selected from methyl and chlorine;

V and Y are each selected independently from hydrogen, methyl and halogen;

Z is selected from —O— and a bond;

m and n are independently selected from 0, 1 and 2, wherein each carbon atom of the resulting carbon chain may be optionally substituted with up to two groups selected independently from $C_{1-6}$alkyl, and the sum of m+n is from 0 to 4;

p is selected from 0 and 1;

q and s are selected from 0, 1 and 2;

r is selected from 0, 1 and 2;

or a pharmaceutically acceptable salt or solvate thereof.

According to a further embodiment of the invention there is provided a compound of formula (IA):

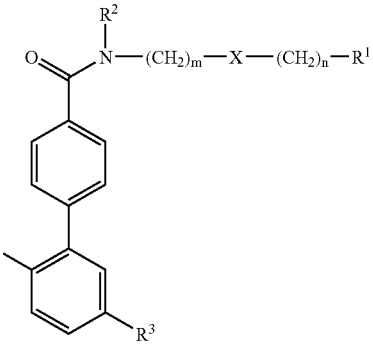

(IA)

wherein $R^1$, $R^2$, $R^3$, m, n and X are as defined above, or a pharmaceutically acceptable salt or solvate thereof.

In a preferred embodiment, the molecular weight of a compound of formula (I) does not exceed 1000, more preferably 800, even more preferably 600.

The group $R^1$ may be optionally substituted by up to three substituents, more preferably one or two substituents, selected from $C_{1-6}$alkyl, $C_{1-6}$alkoxy, oxy, halogen, hydroxy$C_{1-6}$alkyl, —$N(C_{1-6}$alkyl$)_2$, —$CH_2$—$N(C_{1-6}$alkyl$)_2$, —$CO_2C_{1-6}$alkyl, phenyl optionally substituted by halogen and benzyl optionally substituted by halogen and/or cyano.

When X is phenyl, the optional substituents for X are selected independently from $C_{1-6}$alkyl, $C_{1-6}$alkoxy, halogen, trifluoromethyl, trifluoromethoxy, and cyano. Particularly preferred substituents are methyl, chloro, fluoro, cyano, methoxy and trifluoromethoxy. X may also be optionally substituted by $C_{3-7}$cycloalkyl.

In a preferred embodiment, when X is phenyl, $R^1$ is preferably an optionally substituted group selected from pyrrolidinyl, furyl, pyrrolyl, imidazolyl, pyrazolyl, tetrazolyl, oxazolyl, oxadiazolyl, piperidinyl, piperazinyl, morpholino, pyridyl, pyrimidinyl, thienyl, imidazolidinyl, benzimidazolyl and quinolyl. Particularly preferred groups are morpholino, pyrrolidinyl, imidazolyl, pyridyl, oxazolyl, oxadiazolyl, pyrazolyl, piperidinyl, piperazinyl and pyrimidinyl. The optional substituents for $R^1$ when X is phenyl are selected independently from $C_{1-6}$alkyl, $C_{1-6}$alkoxy, oxy, halogen, hydroxy$C_{1-6}$alkyl, —N($C_{1-6}$alkyl)$_2$ and —CH$_2$—N($C_{1-6}$alkyl)$_2$. Particularly preferred optional substituents are methyl and oxy.

In a preferred embodiment, when X is a bond, $R^1$ is selected from an optionally substituted pyrrolidinyl, isoxazolyl, furyl, thienyl, imidazolyl, pyrazolyl, triazolyl, tetrazolyl, oxazolyl, thiazolyl, oxadiazolyl, piperidinyl, piperazinyl, morpholino, pyridyl, tetrahydrofuranyl, tetrahydrothiophenyl and quinolyl. Particularly preferred groups are piperazinyl, piperidinyl, morpholino, imidazolyl, thienyl and pyrrolidinyl. The optional substituents for $R^1$ when X is a bond are selected independently from $C_{1-6}$alkyl, $C_{1-6}$alkoxy, oxy, halogen, hydroxy$C_{1-6}$alkyl, —N($C_{1-6}$alkyl)$_2$, —CH$_2$—N($C_{1-6}$alkyl)$_2$, —CO$_2C_{1-6}$alkyl, phenyl optionally substituted by halogen and benzyl optionally substituted by halogen and/or cyano. Particularly preferred optional substituents are methyl and oxy.

In a preferred embodiment, $R^2$ is selected from hydrogen, $C_{1-4}$alkyl and —CH$_2$-cyclopropyl, more preferably hydrogen.

In a preferred embodiment, $R^4$ is selected from $C_{1-4}$alkyl, cyclopropyl, —CH$_2$-cyclopropyl, pyridinyl and phenyl.

In a preferred embodiment, $R^5$ is selected from hydrogen and $C_{1-4}$alkyl, and phenyl optionally substituted by methyl or halogen.

In a preferred embodiment, $R^6$ is selected from hydrogen and $C_{1-4}$alkyl.

In a preferred embodiment, $R^7$ is selected from $C_{1-4}$alkyl, —NHCOCH$_3$, pyridinyl, pyrimidinyl and oxadiazolyl.

In a preferred embodiment, $R^8$ is hydrogen.
In a preferred embodiment, $R^9$ is $C_{1-4}$alkyl.
In a preferred embodiment, W is methyl.
In a preferred embodiment, V and Y are each selected independently from hydrogen, chlorine and fluorine. In a further preferred embodiment, V is fluorine.

In a preferred embodiment, Z is a bond
In a preferred embodiment, m and n are independently selected from 0, 1 and 2, and the sum of m+n is from 0-3.
In a preferred embodiment, q is selected from 0 and 1.
In a preferred embodiment, s is selected from 0 and 1.
In a preferred embodiment, r is selected from 0 and 1. In particular, r is 0.

It is to be understood that the present invention covers all combinations of particular and preferred groups described hereinabove.

Particular compounds according to the invention include those mentioned in the examples and their pharmaceutically acceptable salts and solvates. A specific example which may be mentioned is:

$N^3$-Cyclopropyl-$N^{4'}$-(3-imidazol-1-ylpropyl)-6-methyl-1,1'-biphenyl-3,4'-dicarboxamide.

Further specific examples which may be mentioned include:

$N^3$-Cyclopropyl-6-methyl-$N^{4'}$-[4-(4-methylpiperazin-1-yl)benzyl]-1,1'-biphenyl-3,4'-dicarboxamide;

$N^3$-Cyclopropyl-6-methyl-$N^{4'}$-(1,3-thiazol-2-ylmethyl)-1,1'-biphenyl-3,4'-dicarboxamide;

$N^3$-Cyclopropyl-5-fluoro-6-methyl-$N^{4'}$-[3-(morpholin-4-ylmethyl)benzyl]-1,1'-biphenyl-3,4'-dicarboxamide;

$N^3$-Cyclopropyl-6-methyl-$N^{4'}$-[3-(morpholinylmethyl)benzyl]-1,1'-biphenyl-3,4'-dicarboxamide;

$N^3$-Cyclopropyl-6-methyl-$N^{4'}$-{2-[(4-methylpiperazin-1-yl)methyl]phenyl}-1,1'-biphenyl-3,4'-dicarboxamide;

tert-Butyl 4-{[({5'-[(cyclopropylamino)carbonyl]-2'-methyl-1,1'-biphenyl-4-yl}carbonyl)amino]methyl}piperidine-1-carboxylate;

$N^3$-Cyclopropyl-6-methyl-$N^{4'}$-[3-(pyrrolidin-1-ylmethyl)benzyl]-1,1'-biphenyl-3,4'-dicarboxamide;

$N^3$-Cyclopropyl-6-methyl-$N^{4'}$-{3-[(4-methylpiperazin-1-yl)methyl]benzyl}1,1'-biphenyl-3,4'-dicarboxamide; and $N^3$-Cyclopropyl-6-methyl-$N^{4'}$-[3-(piperidin-1-ylmethyl)benzyl]-1,1'-biphenyl-3,4'-dicarboxamide.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A $C_{1-4}$alkyl group is preferred, for example methyl, ethyl or isopropyl. The said alkyl groups may be optionally substituted with one or more halogen atoms, in particular fluorine atoms, for example, trifluoromethyl.

As used herein, the term "alkoxy" refers to a straight or branched chain alkoxy group, for example, methoxy, ethoxy, propoxy, prop-2-oxy, butoxy, but-2-oxy, 2-methylprop-1-oxy, 2-methylprop-2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-5}$ cycloalkyl group is preferred, for example cyclopropyl.

As used herein, the terms "heteroaryl ring" and "heteroaryl" refer to an monocyclic five- to seven-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the terms "heterocyclic ring" or "heterocyclyl" refer to a monocyclic three- to seven-membered saturated or non-aromatic, unsaturated hydrocarbon ring containing at least one heteroatom independently selected from oxygen, nitrogen and sulfur. Preferably, the heterocyclyl ring has five or six ring atoms. Examples of heterocyclyl groups include, but are not limited to, aziridinyl, pyrrolinyl, pyrrolidinyl, imidazolinyl, imidazolidinyl, pyrazolinyl, pyrazolidinyl, piperidyl, piperazinyl, morpholino, tetrahydropyranyl, tetrahydrofuranyl, and thiomorpholino. The said ring may be optionally substituted by one or more substituents independently selected from $C_{1-6}$alkyl and oxy.

As used herein, the term "fused bicyclic ring" refers to a ring system comprising two five- to seven-membered saturated or unsaturated rings, the ring system containing at least one heteroatom independently selected from oxygen, nitrogen and sulfur. Preferably, each ring has five or six ring atoms. Examples of suitable fused bicyclic rings include, but are not limited to, naphthyl, indolyl, indolinyl, benzothienyl, quinolyl, isoquinolyl, tetrahydroquinolyl, benzodioxanyl, indanyl and tetrahydronaphthyl. Each ring may be optionally substituted with one or more substituents selected from halogen, $C_{1-6}$alkyl, oxy, —(CH$_2$)$_p$NR$^{10}$R$^{11}$, —CO(CH$_2$)$_p$ $NR^{10}R^{11}$, and imidazolyl. Particularly preferred substituents are chlorine, imidazolyl and —$CH_2$—$N(CH_3)_2$.

As used herein, the terms "halogen" or "halo" refer to the elements fluorine, chlorine, bromine and iodine. Preferred halogens are fluorine, chlorine and bromine. A particularly preferred halogen is fluorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Salts of the compounds of the present invention are also encompassed within the scope of the invention and may, for example, comprise acid addition salts resulting from reaction of an acid with a nitrogen atom present in a compound of formula (I).

Salts encompassed within the term "pharmaceutically acceptable salts" refer to non-toxic salts of the compounds of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

For example, a general method (A) for preparing the compounds of Formula (I) comprises the reactions set out in Scheme 1 below.

Scheme 1

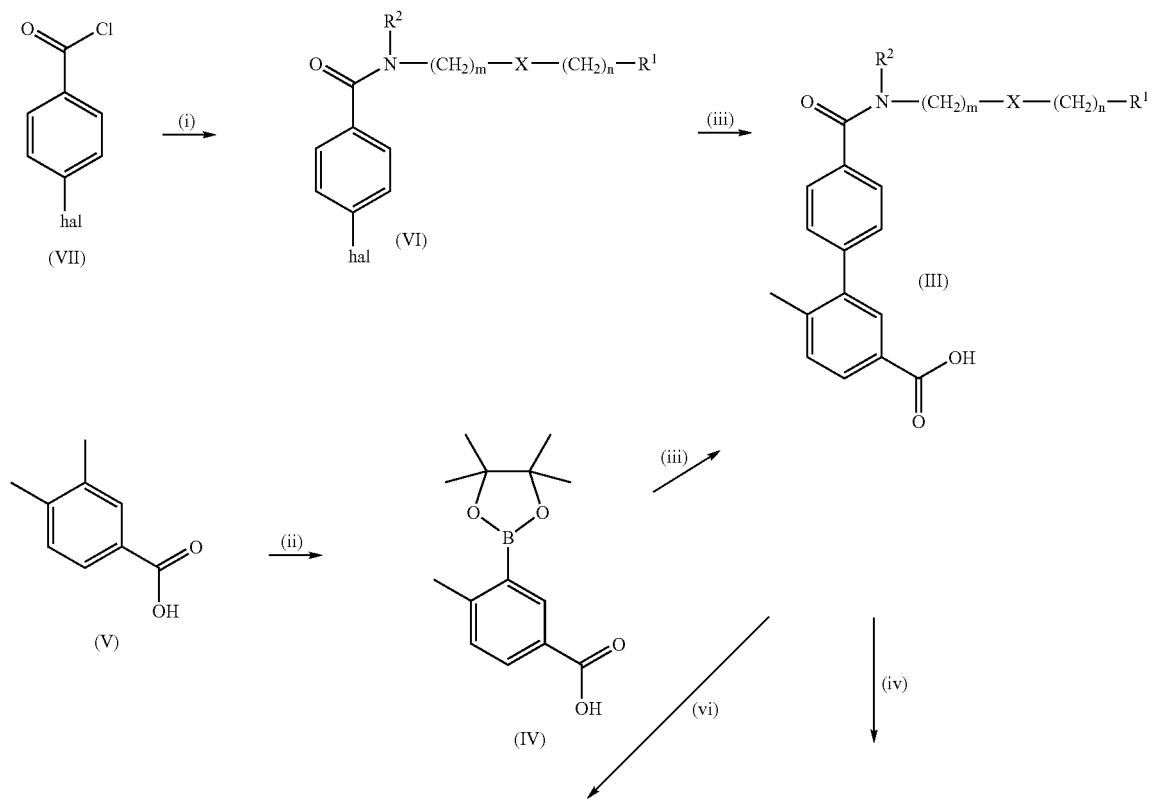

-continued

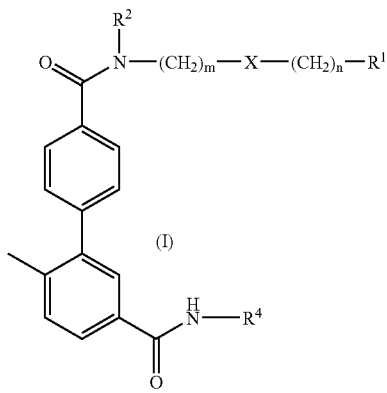

(I)

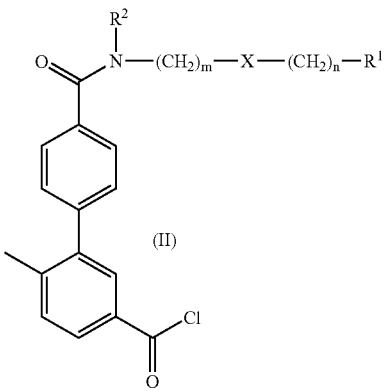

(II)

(i) R¹(CH₂)ₙX(CH₂)ₘN R²H, Et₃N, THF
(ii) Bis(pinnacolato)diboron, PdCl₂dppf, KOAc, DMF
(iii) (Ph₃P)₄Pd, Na₂CO₃, DME
(iv) (COCl)₂, DMF
(v) R⁴NH₂, pyridine
(vi) R₄NH₂, PyBOP, HOBT, DIPEA, DMF For example, a general method (B) for preparing the compounds of Formula (I) comprises the reactions set out in Scheme 2 below.

Scheme 2

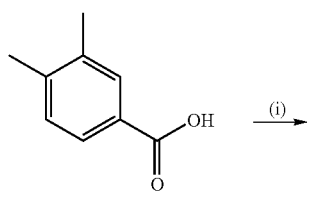

(V)

↓ (i)

(IX)

↓ (ii)

(VIII)

↓ (iii)/(iv)

-continued

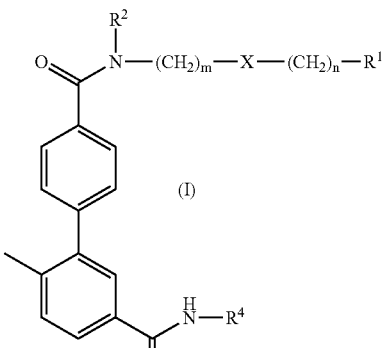

(I)

(i) R⁴NH₂, HATU, HOBT, DIPEA, DMF
(ii) (4-Methoxycarbonylphenyl)boronic acid, Ph₃P)₄Pd, Na₂CO₃, DME
(iii) NaOH, MeOH, H₂O
(iv) R¹(CH₂)ₙX(CH₂)ₘN R²H, HATU, HOBT, DIPEA, THF For example, a general method (C) for preparing the compounds of Formula (I) comprises the reactions set out in Scheme 3 below.

Scheme 3

(XII)   +   (V)   → (i)

-continued

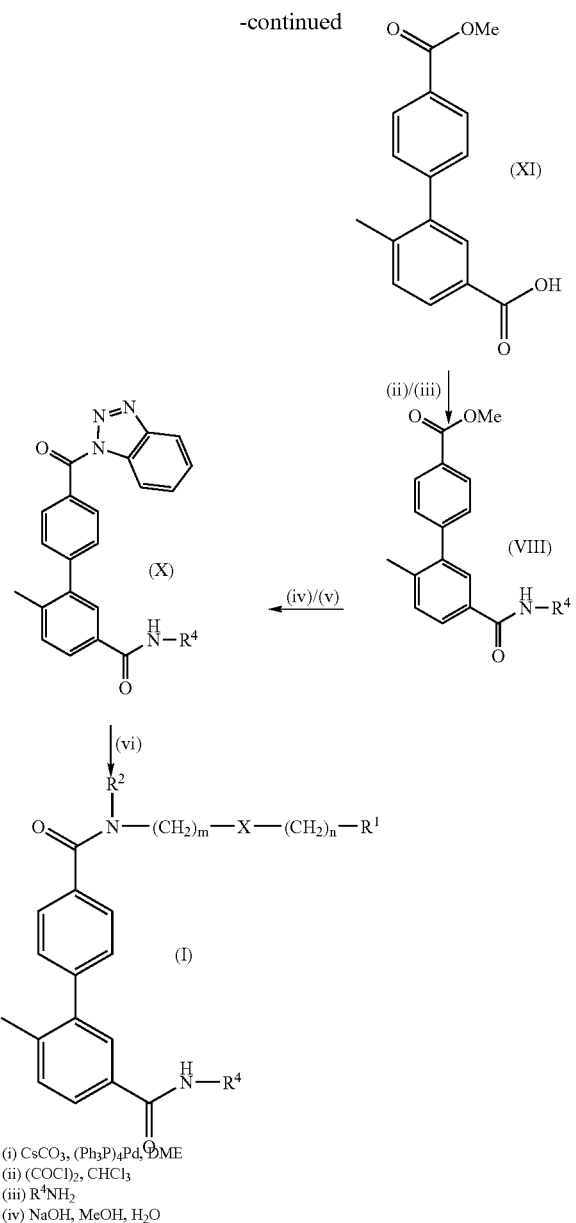

(i) CsCO₃, (Ph₃P)₄Pd, DME
(ii) (COCl)₂, CHCl₃
(iii) R⁴NH₂
(iv) NaOH, MeOH, H₂O
(v) 1-methysulphonylbenzotriazole, Et₃N, THF, DMF
(vi) R¹(CH₂)ₙX(CH₂)ₘN R²H, THF Thus, according to the invention there is provided a process for preparing a compound of formula (I) which comprises:
(a) reacting a compound of formula (XIII)

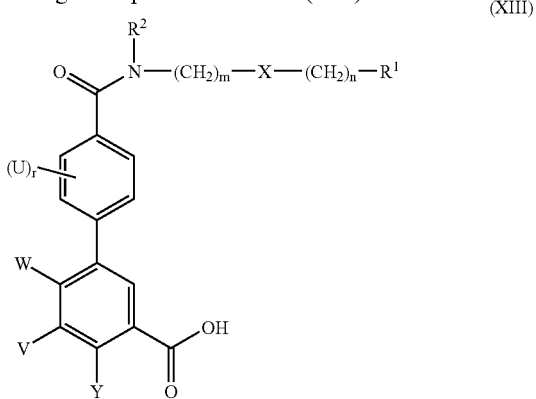

(XIII)

wherein $R^1$, $R^2$, X, U, W, V, Y, m, n and r are as defined above, with a compound of formula (XIV)

$$R^4-(CH_2)_q-NH_2 \quad (XIV)$$

wherein $R^4$ and q are as defined above, under amide forming conditions (if desired, the acid compound (XIII) may be converted to an activated form of the acid, for example the acid chloride, by treatment with, for example, oxalyl chloride, and then the activated acid thus formed reacted with the amine compound (XIV));

(b) reacting a compound of formula (XV)

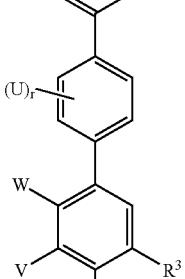

(XV)

wherein $R^3$, U, W, V, Y and r are as defined above, with a compound of formula (XVI)

$$R^1(CH_2)_nX(CH_2)_mNR^2H \quad (XVI)$$

wherein $R^1$, $R^2$, X, m and n are as defined above, under amide forming conditions;

(c) reacting a compound of formula (XVII)

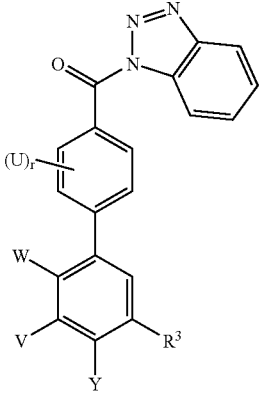

(XVII)

wherein $R^3$, U, W, V, Y and r are as defined above, with a compound of formula (XVI) as defined above; or (d) functional group conversion of a compound of formula (XVIII)

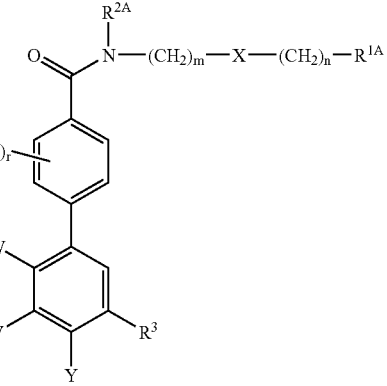

(XVIII)

wherein $R^3$, X, U, W, V, Y, m, n and r are as defined above and $R^{1A}$ and $R^{2A}$ are $R^1$ and $R^2$ as defined above or groups convertible to $R^1$ and $R^2$, to give a compound of formula (I).

Suitable amide forming conditions are well known in the art and include treating a solution of the acid, in for example THF, with an amine in the presence of, for example, HOBT, HATU and DIPEA.

Whilst it is possible for the compounds, salts or solvates of the present invention to be administered as the new chemical, the compounds of formula (I) and their pharmaceutically acceptable salts and solvates are conveniently administered in the form of pharmaceutical compositions. Thus, in another aspect of the invention, we provide a pharmaceutical composition comprising a compound of formula (I) or a pharmaceutically acceptable salt or solvate thereof, in admixture with one or more pharmaceutically acceptable carriers, diluents or excipients.

The compounds of formula (I) and their pharmaceutically acceptable salts and solvates may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable salts and solvates. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken Into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 μg/kg body weight. In most cases they will be administered in one or more doses in an amount not in excess of about 20 mg/kg body weight per day. Preferably, in most cases, dose is from about 100 μg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

In another aspect, the present invention provides a compound of formula (I) or a salt or solvate thereof, for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I) or a pharmaceutically acceptable salt or solvate thereof. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula(I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, neurodegenerative disease, Alzheimer's disease, Parkinson's disease and epilepsy which comprises administering to said subject a therapeutically effective amount of a compound of formula (I) or a pharmaceutically acceptable salt or solvate thereof.

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable salt or solvate thereof.

A further aspect of the invention provides the use of a compound of formula (I), or a pharmaceutically acceptable salt or solvate thereof, for the preparation of a medicament for the treatment of a condition or disease state mediated by p38 kinase activity or mediated by cytokines produced by p38 kinase activity.

A further aspect of the invention provides the use of a compound of formula (I), or a pharmaceutically acceptable salt or solvate thereof, for the preparation of a medicament for the treatment of a condition or disease state selected from rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, and cancer including breast cancer, colon cancer, lung cancer or prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy, and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, neurodegenerative disease, Alzheimer's disease, Parkinson's disease and epilepsy.

A further aspect of the invention provides the use of a compound of formula (I), or a pharmaceutically acceptable salt or solvate thereof, for the preparation of a medicament for the treatment of any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain.

The compounds of formula (I) and their salts, solvates and physiologically functional salts and solvates may be employed alone or in combination with other therapeutic agents for the treatment of the above-mentioned conditions. In particular, in rheumatoid arthritis therapy, combination with other chemotherapeutic or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) or pharmaceutically acceptable salt(s) or solvate(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvate(s) thereof and the other pharmaceutically active agent(s) and the relative timings of administration will be selected in order to achieve the desired combined therapeutic effect. Examples of other pharmaceutically active agents which may be employed in combination with compounds of formula (I) and their salts and solvates for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDS) such as methotrexate, sulphasalazine, cyclosporin A, hydroxychoroquine, auranofin, aurothioglucose, gold sodium thiomalate and penicillamine.

EXAMPLES

The following examples are illustrative embodiments of the invention, not limiting the scope of the invention in any way. Reagents are commercially available or are prepared according to procedures in the literature.

LCMS was conducted on a column (3.3 cm×4.56 mm ID, 3 um ABZ+PLUS), at a Flow Rate of 3 ml/min, Injection Volume of 5 μl, at room temperature and UV Detection Range at 215 to 330 nm.

General Method A:

Benzoic acid (0.17 mmol), HATU (0.2 mmol), HOBT (0.17 mmol), DIPEA (0.51 mmol), and amine (0.2 mmol) were mixed in DMF (2 ml) and the reaction stirred at room temperature for 24 h. Further portions of amine (0.05 mmol) and HATU (0.052 mmol) were added and the mixture heated for 18 h at 60° C. The solvent was evaporated under vacuum and the residue partitioned between DCM (5 ml) and aqueous sodium carbonate (1M, 5 ml). The organic phase was reduced to dryness under vacuum and the amide purified as specified in the example.

Example 1

$N^3$-Cyclopropyl-6-methyl-$N^{4'}$-(4-methylpiperazin-1-yl)-1,1'-biphenyl-3,4'-dicarboxamide a) $N^3$-Cyclopropyl-6-methyl-$N^{4'}$-(4-methylpiperazin-1-yl)-1,1'-biphenyl-3,4'-dicarboxamide was synthesised from 3'-[(cyclopropylamino)carbonyl]-6'-methyl-1,1'-biphenyl-4-yl)carboxylic acid and 1-methylpiperazine using method A. Purified by chromatography on an SPE (silica, 5 g) eluting with a DCM/ethanol/ammonia gradient (500:8:1 to 40:8:1). NMR: ∂H [$^2$H$_6$]-DMSO 8.42,(1H, d), 7.75,(1H, dd), 7.69, (1H, d), 7.46,(2H, d), 7.43,(2H, d), 7.38,(1H, d), 3.62,(2H, b), 2.84,( 2.32,(6H, b), 2.27,(3H, s), 2.20,(3H, s), 0.67,(2H, m), 0.55,(2H, m). LCMS: retention time 2.10 min, MH$^+$378.

b) 3'-[(Cyclopropylamino)carbonyl]-6'-methyl-1,1'-biphenyl-4-yl)carboxylic acid

Methyl 3'-[(cyclopropylamino)carbonyl]-6'-methyl-1,1'-biphenyl-4-yl)carboxylate (2.7 g, 8.7 mmol) and lithium hydroxide monohydrate (0.77 g, 18.3 mmol) were mixed in THF (20 ml) and water (10 ml) and heated at 80° C. for 2 h. The THF was evaporated under vacuum and hydrochloric acid (2N) added to the aqueous with vigorous stirring. The solid produced was filtered off, dissolved in methanol and absorbed onto silica. Purified by flash column chromatography eluting with DCM/ethanol/ammonia (20:8:1). The product fractions were concentrated under vacuum to give 3'-[(cyclopropylamino)carbonyl]-6'-methyl-1,1'-biphenyl-4-yl)carboxylic acid (2.0 g, 78%).

LCMS: retention time 2.94 min, MH$^+$296.

c) Methyl 3'-[(cyclopropylamino)carbonyl]-6'-methyl-1,1'-biphenyl-4-yl)carboxylate N-Cyclopropyl-3-iodo-4-methylbenzamide (4.7 g, 15.6 mmol), (4-methoxycarbonylphenyl)boronic acid (3.4 g, 18.7 mmol), aqueous sodium carbonate (1M, 50 ml) and tetrakis (triphenylphosphine)palladium (1.8 g, 0.156 mmol) in DME (100 ml) were heated at 95° C. for 18 h. The reaction mixture was absorbed onto silica and purified by flash column chromatography eluting with DCM/ethanol/ammonia (500:8:1).

The product fractions were reduced to dryness under vacuum to give methyl 3'-[(cyclopropylamino)carbonyl]-6'-methyl-1,1'-biphenyl-4-yl)carboxylate (2.76 g, 57%).

LCMS: retention time 3.21 min, MH$^+$310.

d) N-Cyclopropyl-3-iodo-4-methylbenzamide

3-Iodo-4-methylbenzoic acid (5 g, 19.1 mmol) and HATU (8.71 g, 22.9 mmol) in DMF (25 ml) were stirred at room temperature for 10 minutes. HOBT (2.58 g, 19.1 mmol), cyclopropylamine (1.37 g, 22.9 mmol) and DIPEA (2.5 ml, 57.3 mmol) were added and stirring continued for 18 h. The DMF was evaporated under vacuum and the residue partitioned between DCM (100 ml) and aqueous sodium carbonate (1M, 75 ml). The aqueous layer was extracted with DCM (50 ml) and the combined organic phases washed with brine (75 ml) and dried (magnesium sulphate). The solution was absorbed onto silica and purified by chromatography on silica eluting with ethyl acetate/cyclohexane (1:3). The product fractions were reduced to dryness under vacuum to give N-cyclopropyl-3-iodo-4-methylbenzamide (4.7 g, 82%). LCMS: retention time 3.09 min, MH$^+$302.

Example 2

N$^3$-Cyclopropyl-N$^{4'}$-(3-imidazol-1-ylpropyl)-6-methyl-1,1'-biphenyl-3,4'-dicarboxamide N$^3$-Cyclopropyl-N$^{4'}$-(3-imidazol-1-ylpropyl)-6-methyl-1,1'-biphenyl-3,4'-dicarboxamide was synthesised from 3'-[(cyclopropylamino)carbonyl]-6'-methyl-1,1'-biphenyl-4-yl)carboxylic acid and 1-(3-aminopropyl)imidazole using method A. Purified by chromatography on silica, eluting with a DCM/ethanol/ammonia gradient (200:8:1 to 75:8:1). NMR: ∂H [$^2$H$_6$]-DMSO 8.58,(1H, t), 8.43,(1H, d), 7.93,(2H, d), 7.75,(1H, dd), 7.68,(1H, d), 7.66,(1H, s), 7.47,(2H, d), 7.38, (1H, d), 7.21,(1H, s), 6.89,(1H, s), 4.03,(2H, t), 3.26,(2H, q), 2.83,(1H, m), 2.26,(3H, s), 1.97,(2H, m), 0.67,(2H, m), 0.55, (2H, m).

LCMS: retention time 2.20 min, MH$^+$403.

Example 3

N$^3$-Cyclopropyl-6-methyl-N$^{4'}$-(3-morpholin-4-ylpropyl)-1,1'-biphenyl-3,4'-dicarboxamide N$^3$-Cyclopropyl-6-methyl-N$^{4'}$-(3-morpholin-4-ylpropyl)-1,1'-biphenyl-3,4'-dicarboxamide was synthesised from 3'-[(cyclopropylamino)carbonyl]-6'-methyl-1,1'-biphenyl-4-yl)carboxylic acid and 4-(3-aminopropyl)morpholine using method A. Purified by chromatography on silica, eluting with a DCM/ethanol/ammonia gradient (200:8:1 to 75:8:1). NMR: ∂H [$^2$H$_6$]-DMSO 8.55,(1H, t), 8.42,(1H, d), 7.91,(2H, d), 7.74,(1H, dd), 7.68,(1H, d), 7.46,(2H, d), 7.38,(1H, d), 3.56, (4H, t), 3.30,(2H, m), 2.83,(1H, m), 2.34,(6H, m), 2.26,(3H, s), 1.69,(2H, m), 0.67,(2H, m), 0.54,(2H, m).

LCMS: retention time 2.28 min, MH$^+$422.

Example 4

N$^3$-Cyclopropyl-6-methyl-N$^{4'}$-[3-(4-methylpiperazin-1-yl)propyl]-1,1'-biphenyl-3,4'-dicarboxamide N$^3$-Cyclopropyl-6-methyl-N$^{4'}$-[3-(4-methylpiperazin-1-yl)propyl]-1,1'-biphenyl-3,4'-dicarboxamide was synthesised from 3'-[(cyclopropylamino)carbonyl]-6'-methyl-1,1'-biphenyl-4-yl)carboxylic acid and 1-(3-aminopropyl)-4-methylpiperazine using method A. Purified by chromatography on silica, eluting with a DCM/ethanol/ammonia gradient (100:8:1 to 40:8:1). NMR: ∂H [$^2$H$_6$]-DMSO 8.56,(1H, t), 8.42,(1H, d), 7.91,(2H, d), 7.74,(1H, dd), 7.68, (1H, d), 7.45,(2H, d), 7.38,(1H, d), 3.30,(2H, m), 2.83,(1H, m), 2.48-2.17, (13H, bm), 2.14,(3H, s), 1.68,(2H, m), 0.67, (2H, m), 0.54,(2H, m).

LCMS: retention time 2.2 min, MH$^+$435.

Example 5

N$^{4'}$-(3-Imidazol-1-ylpropyl)-6-methyl-N$^3$-propyl-1,1'-biphenyl-3,4'-dicarboxamide a) 5'-[(1H-1,2,3-Benzotriazol-1-yl)carbonyl]-2'-methyl-N-propyl-1,1'-biphenyl-3-carboxamide (25 mg, 0.0'mmol) in THF (1 ml) was mixed with 1-(3-aminopropyl)imidazole (7.2 µl) in THF (0.6 ml) and the reaction stirred at room temperature for 4 h. The reaction was loaded onto an SPE (aminopropyl, 1 g) and eluted with chloroform, ethyl acetate and methanol. The methanol fraction was applied to an SPE (SCX, 0.5 g), washed with methanol and eluted with methanol/ammonia. The solvent was evaporated from the methanol/ammonia fractions to give N$^{4'}$-(3-imidazol-1-ylpropyl) methyl-N$^3$-propyl-1,1'-biphenyl-3,4'-dicarboximide. NMR: ∂H CDCl$_3$ 7.82,(2H, d), 7.67,(1H, dd), 7.62,(1H, d), 7.47, (1H, s), 7.40,(1H, t), 7.32-7.28,(3H, m), 7.03,(1H, s), 6.97, (1H, s), 6.70,(1H, t), 4.05,(2H, m), 3.48,(2H, q), 3.39,(2H, q), 2.12,(2H, m), 1.62,(2H, m), 0.96,(3H, t). LCMS: retention time 2.33 min, MH$^+$405.

b) 4'-[(1H-1,2,3-Benzotriazol-1-yl)carbonyl]-6-methyl-N-propyl-1,1'-biphenyl-3-carboxamide 6'-Methyl-3'-[(propylamino)carbonyl]-1,1'-biphenyl-4-carboxylic acid (121 mg, 0.41 mmol), triethylamine (100 µl) and 1-(methylsulphonyl)-1H-benzotriazole (119 mg, 0.6 mmol) were mixed in THF (3 ml) and DMF (0.5 ml) and heated at reflux for 3 h. The reaction was concentrated under vacuum and partitioned between chloroform (5 ml) and water (5 ml). The aqueous was washed with chloroform (3 ml) and the combined organics reduced to dryness under vacuum. The residue was chromatographed on an SPE (silica, 5 g) eluting with chloroform, ether and ethylacetate, which after evaporation of the solvent under vacuum gave 4'-[(1H-1,2,3benzotriazol-1-yl)carbonyl]-6-methyl-N-propyl-1,1'-biphenyl-3-carboxamide (150 mg).

c) 6'-Methyl-3'-[(propylamino)carbonyl]-1,1'-biphenyl-4-carboxylic acid

Methyl 6'-methyl-3'-[(propylamino)carbonyl]-1,1'-biphenyl-4-carboxylate (216 mg, 0.7 mmol) in methanol (4 ml) was mixed with aqueous sodium hydroxide (2N, 1 ml) and stirred at room temperature for 2 h. The methanol was evaporated, the reaction diluted with water (4 ml) and extracted with chloroform (2×5 ml). The aqueous was acidified with hydrochloric acid (2N, 2 ml) and extracted with chloroform (2×6 ml). Both sets of organic extracts were combined in methanol (4 ml) and stirred with aqueous sodium hydroxide (2N, 2 ml) for 3 h. The methanol was evaporated, the reaction diluted with water (4 ml) and washed with chloroform (2×5 ml). The aqueous was acidified with hydrochloric acid (2N, 2 ml) and extracted with chloroform (2×6 ml). The solvent was evaporated from the organic extracts to give 6'-methyl-3'-[(propylamino)carbonyl]-1,1'-biphenyl-4-carboxylic acid (121 mg). NMR: ∂H CDCl$_3$ 8.13,(2H, d), 7.69,(1H, dd), 7.62,(1H, d), 7.41,(2H, d), 7.35,(1H, d), 3.42,(2H, t), 2.30,(3H, s), 1.64, (2H, m), 0.99,(3H, t).

d) Methyl 6'-methyl-3'-[(propylamino)carbonyl]-1,1'-biphenyl-4-carboxylate

4'-(Methoxycarbonyl)-6-methyl-1,1'-biphenyl-3-carboxylic acid (190 mg, 0.7 mmol) and oxalyl chloride (70 µl, 0.77 mol) in chloroform (4 ml) were stirred at room temperature for 15 min. Propylamine (200 µl) was added and stirring continued for 45 min. The reaction was quenched with water (4 ml), the phases separated and the organic phase passed through an aminopropyl SPE eluting with chloroform. After evaporation of the solvent this gave methyl 6'-methyl-3'-[(propylamino)carbonyl]-1,1'-biphenyl-4-carboxylate (216 mg). LCMS: retention time 3.26 min, MH$^+$312.

e) 4'-(Methoxycarbonyl)-6-methyl-1,1'-biphenyl-3-carboxylic acid

3-Iodo-4-methylbenzoic acid (8.7 g, 33.3 mmol), (4-methoxycarbonylphenyl)boronic acid (6.0 g, 33.3 mmol), caesium carbonate (1 0.8 g, 33.3 mmol) and tetrakis(triphenylphosphine)palladium (1.92 g, 1.∂mmol) in DME (120 ml) were heated at 90° C. for 6 h. The cooled reaction mixture was filtered and the residue washed with DME. The combined filtrate and washings were absorbed onto silica and chromatographed on a silica flash column eluting with DCM/ethanol/ammonia (40:8:1 then 30:8:1). The product fractions were reduced to dryness under vacuum to give 4'-(methoxycarbonyl)-6-methyl-1,1'-biphenyl-3-carboxylic acid (2.28 g, 25%). LCMS: retention time 3.22 min, [M–H]$^-$269.

f) 1-(Methylsulphonyl)-1H-benzotriazole

Methanesulphonyl chloride (9.3 ml, 0.12 mol) in toluene (30 ml) was added dropwise to a solution of benzotriazole (11.9 g, 0.1 mol) and pyridine (12 ml, 0.16 mol) in toluene (120 ml). The reaction was stirred at room temperature for 20 h, diluted with ethyl acetate (150 ml), washed with water (2×100 ml), brine (150 ml) and dried (magnesium sulphate). The solvent was evaporated under vacuum to give 1-(methylsulphonyl)-1H-benzotriazole (19 g). NMR: ∂H CDCl$_3$ 8.17,(1H, m), 8.02,(1H, m), 7.69,(1H, m), 7.55,(1H, m), 3.52, (3H, s).

Example 6

N$^3$-Cyclopropyl-6-methyl-N$^{4'}$-[4-(4-methylpiperazin-1-yl)benzyl]-1,1'-biphenyl-3,4'-dicarboxamide Example 7

N$^3$-Cyclopropyl-6-methyl-N$^{4'}$-(1,3-thiazol-2-ylmethyl)-1,1'-biphenyl-3,4'-dicarboxamide Example 8

N$^3$-Cyclopropyl-6-methyl-N$^{4'}$-{3-[(4-methylpiperazin-1-yl)methyl]phenyl}-1,1'-biphenyl-3,4'-dicarboxamide General Method B:

HATU (65 mg, 0.17 mmol) was added to a solution of {3'-[(cyclopropylcarbonyl)amino]-6'-methyl-biphen-4-yl}carboxylic acid (50 mg, 0.17 mmol) in DMF (2 ml). After 5 minutes HOBT (23 mg, 0.17 mmol), the chosen amine (0.17 mmol) and DIPEA (0.087 ml, 0.51 mmol) were added and the reaction mixture stirred at room temperature under nitrogen for 18 hours. The DMF was removed in vacuo and the residue partitioned between DCM (5 ml) and aqueous sodium carbonate (1M, 5 ml). The layers were separated and the organic layer purified by SPE cartridge (Si, 5 g) eluting in turn with DCM, chloroform, ether, ethyl acetate, acetonitrile, acetone, ethanol and DCM:ethanol:ammonia (40:8:1, 20:8:1, 10:8:1) to give the desired products.

| Compound | Amine | MH$^+$ | Retention time (minutes) |
|---|---|---|---|
| Example 6 | 1-methyl-4-(4-aminomethylphenyl)piperazine | 483 | 2.37 |
| Example 7 | 2-aminomethylthiazole | 392 | 2.88 |
| Example 8 | 1-(3-aminobenzyl)-4-methylpiperazine | 483 | 2.50 |

Example 9

N$^3$-Cyclopropyl-5-fluoro-6-methyl-N$^{4'}$-[3-(morpholin-4-ylmethyl)benzyl]-1,1'-biphenyl-3,4'-dicarboxamide {3'-[(Cyclopropylamino)carbonyl]-5'-fluoro-6'-methyl-1,1'-biphen-4-yl}carboxylic acid (Intermediate 1, 31 mg, 0.10 mmol), 1-(3-dimethylaminopropyl)-3-ethylcarbodiimide hydrochloride (21 mg, 0.11 mmol), HOBT (15 mg, 0.11 mmol) and 4(3-aminomethylbenzyl)morpholine (Intermediate 3, 0.11 mmol) were dissolved in DMF (4 ml). DIPEA (19 µl, 0.11 mmol) was added to the solution which was then stirred for 5 hours at 40° C. Ethyl acetate (25 ml) and water (25 ml) were added. The ethyl acetate layer was separated and washed sequentially with saturated sodium hydrogen carbonate and hydrochloric acid (0.5M). The solvent was removed in vacuo and the residue was purified by mass-directed HPLC to give N$^3$-cyclopropyl-5-fluoro-6-methyl-N$^{4'}$-[3-(morpholin-4-ylmethyl)benzyl]-1,1'-biphenyl-3,4'-dicarboxamide.

LCMS: MH$^+$502, 3.02 minutes.

(a) {3'-[(Cyclopropylamino)carbonyl]-5'-fluoro-6'-methyl-1,1'-biphen-4-yl}carboxylic acid (Intermediate 1)

3-Bromo-N-cyclopropyl-5-fluoro-4-methylbenzamide (Intermediate 2, 120 mg, 0.45 mmol), 4-(4,4,5,5-tetramethyl-1,3,2-dioxaborolan-2-yl)benzoic acid (111 mg, 0.45 mmol) and tetrakis(triphenylphosphine) palladium (51 mg, 0.045 mmol) were dissolved in DME (3 ml) and aqueous sodium carbonate (1M, 450 µl) was added. The mixture was refluxed at 80° C. for 16 hours. Solvent was removed in vacuo and the residue was purified by silica biotage chromatography, eluting with 2:1 ethyl acetate:cyclohexane followed by 9:1 ethyl acetate:methanol. To give {3'-[(cyclopropylamino)carbonyl]-5'-fluoro-6'-methyl-1,1'-biphen-4-yl}carboxylic acid (129 mg, 91%).

LCMS: MH$^+$314, retention time 3.06 min.

(b) 3-Bromo-N-cyclopropyl-5-fluoro-4-methylbenzamide (Intermediate 2)

3-Fluoro4-methylbenzoic acid (462 mg, 3.0 mmol) was added to a stirred mixture of bromine (2.31 ml, 45 mmol) and iron powder (252 mg, 4.5 mmol) under nitrogen. The reaction was stirred at 20° C. for 4 hours and then left to stand for 16 hours. Sodium thiosulphate solution (200 ml) was added and the product was extracted into ethyl acetate (3×150 ml). Ethyl acetate extracts were combined and evaporated in vacuo. The crude product (mixture of isomers) was dissolved in DMF (7 ml). Cyclopropylamine (208 µl, 3.0 mmol), HOBT (405 mg, 3.0 mmol), 1-(3-dimethylaminopropyl)-3-ethylcarbodiimide hydrochloride (575 mg, 3.0 mmol) and DIPEA (525 µl, 3.0 mmol) were added to the stirred solution. The reaction was stirred for 5 hours at 20° C. Solvent was removed in vacuo and the residue was partitioned between ethyl acetate and water. Combined ethyl acetate extracts were washed sequentially with aqueous sodium hydrogen carbonate and hydrochloric acid (0.5M), then dried (magnesium sulphate). The ethyl acetate was evaporated in vacuo and the residue was purified by silica biotage chromatography eluting with cyclohexane:ethyl acetate (6:1)to give 3-bromo-N-cyclopropyl-5-fluoro-4-methylbenzamide (359 mg, 44%). NMR: $\partial$H-CDCl$_3$ 7.68, (1H, s), 7.39,(1H, d), 6.19,(1H, bs), 2.88,(1H, m), 2.36,(3H, d), 0.88,(2H, m), 0.63,(2H, m). LCMS: MH$^+$272/274, retention time 3.12 min.

(c) 4-(3-Aminomethylbenzyl)morpholine (Intermediate 3)

A solution of N-tert-butyloxycarbonyl-3-(4-morpholinylmethylbenzyl)-carbamic acid tert-butyl ester (Intermediate 4, 1.8 g) in hydrogen chlorine in dioxane (4N) was stirred at room temperature for 2 hours. The solvent was evaporated under vacuum and the residue partitioned between water (10 ml) and ethyl acetate (10 ml). The organic phase was extracted with water (5 ml) and the combined aqueous phases basified with sodium hydroxide (2N). The aqueous was extracted with ethyl acetate (3×10 ml) and the organic extracts combined, dried (magnesium sulphate) and the solvent evaporated in vacuo to give 3-(4-morpholinylmethyl)benzylamine (370 mg).

NMR; $\partial$H-CDCl$_3$ 7.44-7.16,(4H, m), 3.93-3.46,(8H, m),2.47,(4H, m). MS: MH$^+$207.

(d) N-tert-Butyloxycarbonyl-3-(4-morpholinylmethylbenzyl)-carbamic acid tert-butyl ester (Intermediate 4)

Morpholine (2.3 ml) was added to a solution of (3-chloromethyl-benzyl)-carbamic acid tert-butyl ester (Intermediate 5, 1.7 g) in THF (20 ml) and the mixture heated at reflux under nitrogen for 6 hours. Concentration of the reaction under vacuum gave N-tert-butyloxycarbonyl-3-(4-morpholinylmethyl)benzylamine (1.94 g).

NMR; $\partial$H-CDCl$_3$ 7.41-7.16,(4H, m), 4.91,(1H, b), 4.42, (2H, b), 3.72,(4H, m), 3.50,(2H, s), 2.45,(4H, m), 1.5,(9H, s). MS: MH$^+$307.

(e) (3-Chloromethylbenzyl)-carbamic acid tert-butyl ester (Intermediate 5)

Triethylamine (21.27 ml, 152.6 mmol) was added to a suspension of 3-chloromethylbenzylamine hydrochloride (Intermediate 6, 167.92 mmol) in dry THF (180 ml). A solution of di-tert-butyl dicarbonate (14.75 g, 67.58 mmol) in dry THF (50 ml). was added dropwise at 0° C. Once the addition was complete, the reaction mixture was stirred at room temperature for 18 hours. The mixture was filtered and the filtrate concentrated in vacuo. The residue was dissolved in ethyl acetate (250 ml) and washed with water (150 ml). The aqueous layer was extracted with ethyl acetate (50 ml). The combined organic extracts were washed with cold hydrochloric acid (1N, 80 ml), aqueous sodiumhydrogen carbonate solution (100 ml), dried (magnesium sulphate), filtered and concentrated in vacuo to give (3-Chloromethylbenzyl)-carbamic acid tert-butyl ester (12 g, 46.9 mmol).

MS: MNH$_4^+$273.

(f) 3-Chloromethylbenzylamine hydrochloride (Intermediate 6)

Hexamethylenetriamine (27.13 g, 0.194 mol) was added to a solution of dichloro-m-xylene (34 g, 0.194 mol) in chloroform (230 ml) and the mixture heated at reflux for 30 minutes. The cooled reaction was filtered and the filtrate reduced to dryness under vacuum. The residue was dissolved in ethanol (340 ml), treated with concentrated hydrochloric acid (32 ml) and heated at reflux for 3 hours. The reaction was reduced to 4 ml under vacuum, diluted with ether (250 ml) and filtered to give 3-chloromethylbenzylamine hydrochloride (10.57 g).

MS: MH$^+$156.

Example 10

N$^3$-Cyclopropyl-6-methyl-N$^{4'}$-[3-(morpholin-4-ylmethyl)benzyl]-1,1'-biphenyl-3,4'-dicarboxamide Example 11

N$^3$-Cyclopropyl-6-methyl-N$^{4'}$-(2-[(4methylpiperazin-1-yl)methyl]phenyl}-1,1'-biphenyl-3,4'-dicarboxamide Example 12 tert-Butyl 4-{[({5'-[(cyclopropylamino)carbonyl]-2'-methyl-1,1'-biphenyl-4-yl}carbonyl)amino]methyl}piperidine-1-carboxylate Example 13

N$^3$-Cyclopropyl-6-methyl-N$^{4'}$-[2-(4-methylpiperazin-1-yl)phenyl]-1,1'-biphenyl-3,4'-dicarboxamide Example 14

N$^3$-Cyclopropyl-6-methyl-N$^{4'}$-[3-(4-methylpiperazin-1-yl)phenyl]-1,1'-biphenyl-3,4'-dicarboxamide General Method C:

HATU (65 mg, 0.17 mmol) was added to a solution of {3'-[(cyclopropylcarbonyl)amino]-6'-methyl-biphenyl}carboxylic acid (50 mg, 0.17 mmol) in DMF (2 ml). After 5 minutes HOBT (23 mg, 0.17 mmol), the amine (0.17 mmol) and DIPEA (0.087 ml, 0.51 mmol) were added and the reaction mixture stirred at room temperature under nitrogen for 18 hours. The reaction was partitioned between ethyl acetate (50 ml) and hydrochloric acid (1M, 50 ml). The organic phase was washed with aqueous sodium carbonate (1M, 50 ml) and brine (25 ml), dried (magnesium sulphate), and the solvent removed in vacuo. The crude material was purified by Biotage cartridge (Si, 8 g) eluting with a toluene:ethanol gradient (95:5 to 70:30) to yield the desired products.

| Compound | Amine | MH$^+$ | Retention time (minutes) |
| --- | --- | --- | --- |
| Example 10 | 4-(3-aminomethylbenzyl)morpholine | 484 | 2.42 |
| Example 11 | 1-(2-aminobenzyl)-4-methylpiperazine | 483 | 2.43 |
| Example 12 | 4-(aminomethyl)piperidine-1-carboxylic acid tert-butyl ester | 492 | 3.31 |
| Example 13 | 1-(2-aminophenyl)-4-methylpiperazine | 469 | 2.44 |
| Example 14 | 1-(3-aminophenyl)-4-methylpiperazine | 469 | 2.41 |

Example 15

N$^3$-Cyclopropyl-6-methyl-N$^{4'}$-[3-(pyrrolidin-1-ylmethyl)benzyl]-1,1'-biphenyl-3,4'-dicarboxamide Example 16

N$^3$-Cyclopropyl-6-methyl-N$^{4'}$-{(3-[(4-methylpiperazin-1-yl)methyl]benzyl}-1,1'-biphenyl-3,4'-dicarboxamide

Example 17

N³-Cyclopropyl-6-methyl-N⁴'-[4-(morpholin-4-ylmethyl)benzyl]-1,1'-biphenyl-3,4'-dicarboxamide

Example 18

N³-Cyclopropyl-6-methyl-N⁴'-{4-[(4-methylpiperazin-1-yl)methyl]benzyl}-1,1'-biphenyl-3,4'-dicarboxamide

Example 19

N³-Cyclopropyl-6-methyl-N⁴'-(pyridin-4-ylmethyl)-1,1'-biphenyl-3,4'-dicarboxamide

Example 20

N³-Cyclopropyl-6-methyl-N⁴'-[4-(piperidin-1-ylmethyl)benzyl]-1,1'-biphenyl-3,4'-dicarboxamide

Example 21

N³-Cyclopropyl-6-methyl-N⁴'-[4-(pyrrolidin-1-ylmethyl)benzyl]-1,1'-biphenyl-3,4'-dicarboxamide

Example 22

N³-Cyclopropyl-N⁴'-[3-(1H-imidazol-1-ylmethyl)phenyl]-6-methyl-1,1'-biphenyl-3,4'-dicarboxamide

Example 23

N³-Cyclopropyl-6-methyl-N⁴'-[3(piperidin-1-ylmethyl)benzyl]-1,1-biphenyl-3,4'-dicarboxamide

Example 24

N³-Cyclopropyl-6-methyl-N⁴'-(tetrahydrofuran-2-ylmethyl)-1,1'-biphenyl-3,4'-dicarboxamide General Method D:

A solution of {3'-[(cyclopropylamino)carbonyl]-6'-methyl-1,1'-biphen-4-yl}carboxylic acid (50 mg, 0.17 mmol) in DMF (1 ml) was treated with HATU (65 mg, 0.17 mmol) at room temperature. After 5 minutes this was added to a solution of the amine (0.17 mmol) and HOBT (23 mg, 0.17 mmol) in DMF (1 ml). DIPEA (87 ul, 3 eq) was added. The reaction mixture was left at room temperature for 16 hrs, then concentrated in vacuo. The residue was dissolved in DCM (1 ml) and loaded onto a SPE cartridge (1 g, aminopropyl) which had been pre-equilibrated with DCM. Residual sample was washed on with another portion of DCM (0.5 ml), The cartridge was then eluted with: DCM (1×2.5 ml), chloroform (1×2.5 ml), ethyl acetate (1×2.5 ml), and methanol (1×2.5 ml). The fractions containing product were isolated by evaporation to give the desired product.

| Compound | Amine | MH⁺ | Retention time (minutes) |
|---|---|---|---|
| Example 15 | 1-(3-aminomethylbenzyl)pyrrolidine | 468 | 2.48 |
| Example 16 | 1-(3-aminomethylbenzyl)-4-methylpiperazine | — | 2.44 |
| Example 17 | 4-(4-aminomethylbenzyl)morpholine | 484 | 2.42 |
| Example 18 | 1-(4-aminomethylbenzyl)-4-methylpiperazine | 497 | 2.42 |
| Example 19 | 4-aminomethylpyridine | 386 | 2.36 |
| Example 20 | 1-(4-aminomethylbenzyl)piperidine | 482 | 2.49 |
| Example 21 | 1-(4-aminomethylbenzyl)pyrrolidine | 468 | 2.45 |
| Example 22 | 3-(1H-imidazol-1-ylmethyl)aniline | 451 | 2.52 |
| Example 23 | 1-(3-aminomethylbenzyl)piperidine | 482 | 2.52 |
| Example 24 | 2-(aminomethyl)tetrahydrofuran | 379 | 2.85 |

Example 25

N³-Cyclopropyl-N⁴'-({5-[(dimethylamino)methyl]-2-furyl}methyl)-6-methyl-1,1'-biphenyl-3,4'-dicarboxamide HATU (65 mg, 0.17 mmol) was added to a solution of {3'-[(cyclopropylcarbonyl)amino]-6'-methyl-biphen-4-yl}carboxylic acid (50 mg, 0.17 mmol) in DMF (1 ml). After 5 minutes HOBT (23 mg, 0.17 mmol), 2-aminomethyl-5-(dimethylaminomethyl)furan oxalic acid salt (68 mg, 0.204 mmol) and DIPEA (0.087 ml, 0.51 mmol) were added and the reaction mixture stirred at room temperature under nitrogen for 18 hours. The DMF was removed in vacuo and the residue partitioned between DCM (10 ml) and aqueous sodium carbonate (1 M, 10 ml). The organic phase wwas reduced to dryness under vacuum and purified by SPE cartridge (Si, 10 g) eluting in turn with DCM, ether, ethyl acetate, acetonitrile, acetone and ethanol to give the N³-cyclopropyl-N⁴'-({5-[(dimethylamino)methyl]-2-furyl}methyl)-6-methyl-1,1'-biphenyl-3,4'-dicarboxamide (35 mg, 0.081 mmol).

NMR: $\partial$H [²H₆]-DMSO 9.05,(1H, bt,), 8.43,(1H, bd), 7.9,(2H, d) 7.77,(1H, dd), 7.70,(1H, d), 7.48,(2H, d), 7.39,(1H, d), 6.20,(2H, dd), 4.46,(2H, d), 3.36,(2H, s), 2.85,(1H, m), 2.27,(3H, s), 2.12,(6H, s), 0.72-0.52,(4H,2xm). LC/MS: MH⁺432, retention time 2.31 minutes.

Example 26

N³-Cyclopropyl-6-methyl-N⁴'-(piperidin-4-ylmethyl)-1,1'-biphenyl-3,4'-dicarboxamide Trifluoroacetic acid (1 ml) and 1 drop of water were added to tert-butyl 4-{[({5'-[(cyclopropylamino)carbonyl]-2'-methyl-1,1'-biphenyl-4-yl}carbonyl)amino]methyl}piperidine-1-carboxylate (19 mg, 0.038 mmol) and the solution stirred at room temperature under nitrogen for 1 hour. The trifluoroacetic acid was removed in vacuo and the residue partitioned between ethyl acetate (5 ml) and aqueous sodium carbonate (1 M, 5 ml). The layers were separated and the aqueous layer extracted with ethyl acetate (2×5 ml). The organic extracts were washed with brine (10 ml), dried (magnesium sulphate) and concentrated in vacuo to give N~3~-cyclopropyl-6-methyl-N~4~'-(piperidin-4-ylmethyl)-1,1'-biphenyl-3,4'-dicarboxamide (8 mg, 0.020 mmol).

NMR: $\partial$H [²H₆]-DMSO 8.56,(1H, bt), 8.44,(1H, bd), 7.92,(2H, d) 7.77,(1H, dd), 7.69,(1H, d), 7.48,(2H, d), 7.39,(1H, d), 3.16,(2H, bt), 3.02,(2H, bdt), 2.84,(1H, m) 2.52,(2H, m), 2.28,(3H, s), 1.22-1.12,(3H, bm), 1.75-1.63,(3H,m+bd), 0.69-0.52,(4H, 2xm). LC/MS: MH+392, retention time 2.26 minutes.

Abbreviations

DCM Dichloromethane

DIPEA N,N-Diisopropylethylamine

DME Dimethoxyethane

DMF Dimethylformamide

DMSO Dimethylsulphoxide

HATU O-(7-Azabenzotriazol-1-yl)-N,N,N',N'-tetramethyluronium hexafluorophosphate HBTU O-Benzotriazol-1-yl-N,N,N',N'-tetramethyluronium hexafluorophosphate HOBT 1-Hydroxybenzotriazole hydrate PyBOP Benzotriazol-1-yl-oxy-tripyrrolidinophosphonium hexafluorophosphate SPE Solid phase extraction THF Tetrahydrofuran The activity of the compounds of the invention as p38 inhibitors may be demonstrated in the following assays:

p38 Kinase Assay

The peptide substrate used in the p38 assay was biotin-IPTSPITTTYFFFRRR-amide. The p38 and MEK6 proteins were purified to homogeneity from *E.coli* expression systems. The fusion proteins were tagged at the N-terminus with Glutathione-S-Transferase (GST). The maximum activation was achieved by incubating 20 uL of a reaction mixture of 30 nM MEK6 protein and 120 nM p38 protein in the presence of 1.5 uM peptide and 10 mM $Mg(CH_3CO_2)_2$ in 100 mM HEPES, pH 7.5, added to 15 uL of a mixture of 1.5 uM ATP with 0.08 uCi [g-$^{33}$P]ATP, with or without 15 uL of inhibitor in 6% DMSO. The controls were reactions in the presence (negative controls) or absence (positive controls) of 50 mM EDTA. Reactions were allowed to proceed for 60 min at room temperature and quenched with addition of 50 uL of 250 mM EDTA and mixed with 150 uL of Streptavidin SPA beads (Amersham) to 0.5 mg/reaction. The Dynatech Microfluor white U-bottom plates were sealed and the beads were allowed to settle overnight. The plates were counted in a Packard TopCount for 60 seconds. $IC_{50}$ values were obtained by fitting raw data to % I=100*(1-(I-C2)/(C1-C2)), where I was CPM of background, C1 was positive control, and C2 was negative control.

αP38 Fluorescence Polarisation Method

αP38 was prepared in house. SB4777790-R Ligand was diluted in HEPES containing $MgCl_2$, CHAPS, DTT and DMSO. This was added to blank wells of a Black NUNC 384 well plate. αP38 was added to this ligand mixture then added to the remainder of the 384 well plate containing controls and compounds. The plates were read on an LJL Analyst and Fluorescence Anisotropy used to calculate the compound inhibition The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

What is claimed is:

1. A compound of formula (I):

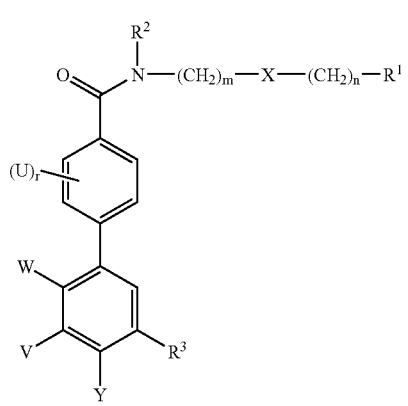

wherein

X is a bond;

$R^1$ is selected from an optionally substituted five- to seven-membered heterocyclic ring, an optionally substituted five- to seven-membered heteroaryl ring and an optionally substituted fused bicyclic ring;

$R^2$ is selected from hydrogen, $C_{1-6}$alkyl and —$(CH_2)_p$—$C_{3-7}$cycloalkyl;

or when X is a bond and m and n are both zero, $R^1$ and $R^2$, together with the nitrogen atom to which they are bound, form a five- to six-membered heterocyclic ring optionally containing one additional heteroatom selected from oxygen and nitrogen, which can be optionally substituted by $C_{1-4}$alkyl;

$R^3$ is the group —CO—NH—$(CH_2)_q$-$R^4$;

when q is 0 to 2 $R^4$ is selected from hydrogen, $C_{1-6}$alkyl, —$C_{3-7}$cycloalkyl, $CONHR^5$, phenyl optionally substituted by $R^7$ and/or $R^8$, heteroaryl optionally substituted by $R^7$ and/or $R^8$ and heterocyclyl optionally substituted by $R^7$ and/or $R^8$;

and when q is 2 $R^4$ is additionally selected from $C_{1-6}$alkoxy, $NHCOR^5$, $NHCONHR^5$, $NR^5R^6$, and OH;

$R^5$ is selected from hydrogen, $C_{1-6}$alkyl and phenyl wherein the phenyl group may be optionally substituted by up to two substituents selected from $C_{1-6}$alkyl and halogen;

$R^6$ is selected from hydrogen and $C_{1-6}$alkyl;

or $R^5$ and $R^6$, together with the nitrogen atom to which they are bound, form a five- to six-membered heterocyclic or heteroaryl ring optionally containing up to one additional heteroatom selected from oxygen, sulfur and nitrogen, wherein the ring may be substituted by up to two $C_{1-6}$alkyl groups;

$R^7$ is selected from $C_{1-6}$alkyl, $C_{1-6}$alkoxy, —$CONR^6R^9$, —$NHCOR^9$, —$SO_2NHR^9$, —$NHSO_2R^9$, halogen, trifluoromethyl, -Z-$(CH_2)_s$—phenyl optionally substituted by one or more halogen atom, -Z-$(CH_2)_s$—heterocyclyl or -Z-$(CH_2)_s$—heteroaryl wherein the heterocyclyl or heteroaryl group may be optionally substituted by one or more substituents selected from $C_{1-6}$alkyl;

$R^8$ is selected $C_{1-6}$alkyl and halogen;

or when $R^7$ and $R^8$ are ortho substituents, then together with the carbon atoms to which they are bound, $R^7$ and $R^8$ may form a five- or six-membered saturated or unsaturated ring to give a fused bicyclic ring system, wherein the ring that is formed by $R^7$ and $R^8$ may optionally contain one or two heteroatoms selected from oxygen, nitrogen and sulfur;

$R^9$ is selected from hydrogen and $C_{1-6}$alkyl;

U is selected from methyl and halogen;

W is selected from methyl and chlorine;

V and Y are each selected independently from hydrogen, methyl and halogen;

Z is selected from —O— and a bond;

m and n are independently selected from 0, 1 and 2, wherein each carbon atom of the resulting carbon chain may be optionally substituted with up to two groups selected independently from $C_{1-6}$alkyl, and the sum of m+n is from 0 to 4;

p is selected from 0 and 1;

q and s are selected from 0, 1 and 2;

r is selected from 0, 1 and 2;

or a pharmaceutically acceptable salt or solvate thereof.

2. A compound according to claim 1 wherein R1 is optionally substituted by up to three substituents selected from $C_{1-6}$alkyl, $C_{1-6}$alkoxy, oxy, halogen, hydroxy$C_{1-6}$alkyl, $N(C_{1-6}$alkyl$)_2$, -CH2—N($C_{1-6}$alkyl$)_2$, —$CO_2C_{1-6}$alkyl, phenyl optionally substituted by halogen and benzyl optionally substituted by halogen and/or cyano.

3. A compound according to claim 1 wherein X is optionally substituted phenyl, and R1 is selected from optionally substituted pyrrolidinyl, furyl, pyrrolyl, imidazolyl, pyrazolyl, tetrazolyl, oxazolyl, oxadiazolyl, piperidinyl, piperazinyl, morpholino, pyridyl, pyrimidinyl, thienyl, imidazolidinyl, benzimidazolyl and quinolyl; wherein the optional substituents for R1 are selected independently from $C_{1-6}$alkyl, $C_{1-6}$alkoxy, oxy, halogen, hydroxy$C_{1-6}$alkyl, —N($C_{1-6}$alkyl$)_2$ and —CH2—N($C_{1-6}$alkyl$)_2$.

4. A compound according to claim 1 wherein X is a bond, and R1 is selected from an optionally substituted pyrrolidinyl, isoxazolyl, furyl, thienyl, imidazolyl, pyrazolyl, triazolyl, tetrazolyl, oxazolyl, thiazolyl, oxadiazolyl, piperidinyl, piperazinyl, morpholino, pyridyl, tetrahydrofuranyl, tetrahydrothiophenyl and quinolyl; wherein the optional substituents for R1 are selected independently from $C_{1-6}$alkyl, $C_{1-6}$alkoxy, oxy, halogen, hydroxy$C_{1-6}$alkyl, —N($C_{1-6}$alkyl$)_2$, —$CH_2$—N($C_{1-6}$alkyl$)_2$, —$CO_2C_{1-6}$alkyl, phenyl optionally substituted by halogen and benzyl optionally substituted by halogen and/or cyano.

5. A compound according to claim 1 wherein $R^2$ is selected from hydrogen, $C_{1-4}$alkyl and —$CH_2$-cyclopropyl.

6. A compound according to claim 1 wherein m and n are independently selected from 0, 1 and 2, and the sum of m+n is from 0-3.

7. A compound according to claim 1 wherein $R^4$ is selected from $C_{1-4}$alkyl, cyclopropyl, —$CH_2$-cyclopropyl, pyridinyl and phenyl.

8. A compound according to claim 1 as defined in any one of Examples 1 to 2, or a pharmaceutically acceptable salt or solvate thereof.

9. A pharmaceutical composition comprising a compound according to claim 1 or a pharmnaceutically acceptable salt or solvate thereof, in admixture with one or more pharmnaceutically acceptable carriers, diluents or excipients.

10. A compound according to claim 2 wherein $R^1$ is an optionally substituted five- to seven-membered heterocyclic ring.

11. A compound according to claim 2 wherein $R^1$ is an optionally substituted five- to seven-membered heteroaryl ring.

12. A compound according to claim 2 wherein $R^1$ is an optionally substituted fused bicyclic ring.

13. A compound according to claim 2 wherein X is optionally substituted phenyl, and $R^1$ is selected from optionally substituted pyrrolidinyl, furyl, pyrrolyl, imidazolyl, pyrazolyl, tetrazolyl, oxazolyl, oxadiazolyl, piperidinyl, piperazinyl, morpholino, pyridyl, pyrimidinyl, thienyl, imidazolidinyl, benzimidazolyl and quinolyl; wherein the optional substituents for $R^1$ are selected independently from $C_{1-6}$alkyl, $C_{1-6}$alkoxy, oxy, halogen, hydroxy$C_{1-6}$alkyl, —N($C_{1-6}$alkyl$)_2$ and —$CH_2$—N($C_{1-6}$alkyl$)_2$.

14. A compound according to claim 2 wherein X is a bond, and $R^1$ is selected from an optionally substituted pyrrolidinyl, isoxazolyl, furyl, thienyl, imidazolyl, pyrazolyl, triazolyl, tetrazolyl, oxazolyl, thiazolyl, oxadiazolyl, piperidinyl, piperazinyl, morpholino, pyridyl, tetrahydrofuranyl, tetrahydrothiophenyl and quinolyl; wherein the optional substituents for $R^1$ are selected independently from $C_{1-6}$alkyl, $C_{1-6}$alkoxy, oxy, halogen, hydroxy$C_{1-6}$alkyl, —N($C_{1-6}$alkyl$)_2$, —$CH_2$—N($C_{1-6}$alkyl$)_2$, —$CO_2C_{1-6}$alkyl, phenyl optionally substituted by halogen and benzyl optionally substituted by halogen and/or cyano.

15. A compound according to claim 2 wherein $R^2$ is selected from hydrogen, $C_{1-4}$alkyl and —$CH_2$-cyclopropyl.

16. A compound according to claim 13 wherein $R^2$ is selected from hydrogen, $C_{1-4}$alkyl and —$CH_2$-cyclopropyl.

17. A compound according to claim 14 wherein $R^2$ is selected from hydrogen, $C_{1-4}$alkyl and —$CH_2$-cyclopropyl.

18. A compound according to claim 2 wherein $R^4$ is selected from $C_{1-4}$alkyl, cyclopropyl, —$CH_2$-cyclopropyl, pyridinyl and phenyl.

19. A compound according to claim 3 wherein $R^4$ is selected from $C_{1-4}$alkyl, cyclopropyl, —$CH_2$-cyclopropyl, pyridinyl and phenyl.

20. A compound according to claim 4 wherein $R^4$ is selected from $C_{1-4}$alkyl, cyclopropyl, —$CH_2$-cyclopropyl, pyridinyl and phenyl.

* * * * *